United States Patent [19]
Gold

[11] Patent Number: 5,342,617
[45] Date of Patent: Aug. 30, 1994

[54] WATER-BASED HUMAN TISSUE LUBRICANT

[75] Inventor: Marvin H. Gold, Sacramento, Calif.

[73] Assignee: Medical Polymers, Inc., Austin, Tex.

[21] Appl. No.: 24,098

[22] Filed: Feb. 26, 1993

Related U.S. Application Data

[63] Continuation of Ser. No. 758,174, Sep. 11, 1991, abandoned, which is a continuation-in-part of Ser. No. 621,305, Dec. 3, 1990, abandoned.

[51] Int. Cl.$^5$ .............................................. A61K 31/74
[52] U.S. Cl. ...................................... 424/405; 424/73; 424/78.02; 424/78.31; 424/78.37; 514/967
[58] Field of Search .................. 424/405, 78.02, 78.31, 424/78.37, 73; 514/967

[56] References Cited

U.S. PATENT DOCUMENTS

| | | | |
|---|---|---|---|
| 2,580,473 | 1/1952 | Sowa et al. | 424/73 X |
| 3,227,652 | 1/1966 | Ackerman et al. | 252/49.5 |
| 3,659,025 | 4/1972 | Halleck | 514/777 |
| 3,699,057 | 10/1972 | Halko et al. | 252/49.3 |
| 3,767,788 | 10/1973 | Rankin | 424/78 |
| 3,811,349 | 5/1974 | Jennings | 424/73 X |
| 4,347,237 | 8/1982 | Evenstad et al. | 424/78 |
| 4,381,293 | 4/1983 | Michel | 424/73 X |
| 4,478,853 | 10/1984 | Chaussee | 514/772 |
| 4,548,812 | 10/1985 | Foley | 424/78.17 |
| 4,551,148 | 11/1985 | Riley, Jr. et al. | 424/DIG. 14 X |
| 4,629,623 | 12/1986 | Balazs et al. | 514/846 X |
| 4,781,847 | 11/1988 | Weitz | 252/49.3 |
| 4,981,686 | 1/1991 | Hardy | 514/873 X |

FOREIGN PATENT DOCUMENTS 675664  12/1963  Canada ................... 424/73

*Primary Examiner*—Thurman K. Page
*Assistant Examiner*—Robert H. Harrison
*Attorney, Agent, or Firm*—Winstead Sechrest & Minick

[57] ABSTRACT

Methods and composition of an improved water based human tissue lubricant are disclosed. The lubricant includes an aqueous solution of high molecular weight polyethyl oxide, a humectant polyol, a sterilizing agent and may include an anti-sticking agent to prevent tackiness on drying. The formulation is ideally suited for use as a vaginal lubricant, as a shaving lubricant and dermatological emollient and as a contact medium for an ultrasonic transducer.

5 Claims, No Drawings

WATER-BASED HUMAN TISSUE LUBRICANT

This is a continuation of application Ser. No. 07/758,174, filed on Sep. 11, 1991, now abandoned, which is a continuation-in-part of application Ser. No. 07/621,305, filed on Dec. 3, 1990, now abandoned.

FIELD OF THE INVENTION

This invention relates to a series of aqueous based lubricants particularly useful in the lubrication of human tissue. More particularly, this lubricant is uniquely capable of replicating the lubricous characteristics of the natural lubricant exuded in the human vagina. Another aspect of this lubricant is that it is also very effective in lubricating the facial tissues and hair on the human face and body so as to enhance shaving comfort.

BACKGROUND OF THE INVENTION

Currently there are a number of lubricating gels, suppositories and fluids available for the purpose of lubricating human tissue. These generally function by supplying water in either a gelled or viscous form, by including a water soluble cellulose derivative (e.g. methyl cellulose, hydroxyethyl cellulose, hydroxypropyl cellulose, sodium carboxymethyl cellulose) or other water soluble polymers such as sodium alginate, polyvinyl pyrrolidone, polyvinyl alcohol, and the like. These systems retain a supply of water which acts as the lubricant but are themselves not very effective lubricants. In other cases the lubricant is supplied as a vaginal suppository which typically contains a polymer of ethylene oxide having a molecular weight of less than 5000, along with a low melting temperature triglyceride or a mineral oil. It is these oily materials which provide the lubricating characteristics and which cause the suppository to melt at body temperature. In the prior aqueous systems, a mineral oil or a triglyceride may also be incorporated by emulsification with an aqueous solution of the cellulose derivative in a composition in which the oily component supplies the lubrication. On the other hand it has been well demonstrated that aqueous solutions of high molecular weight polyethylene oxides provide a slippery feel (see, for example, U.S. Pat. Nos. 3,227,652 and 3,699,057).

SUMMARY OF THE INVENTION

In accordance with the present invention, I have discovered a water based system founded on the use of such high molecular weight polyethylene oxides in combination with a variety of humectant polyols which exhibit a very high degree of lubricity and also act as a tissue conditioner, when applied from an aqueous solution. Specifically the polyethylene oxides I find most applicable are those ranging in molecular weight from 100,000 to 5,000,000. As polyols to be used in my lubricating system, I have found that glycerol, diglycerol, propylene glycol, dipropylene glycol, sorbitol and a variety of commercially available polyols made by the hydrogenation of the higher sugars, or starches, are particularly beneficial. The aqueous solutions of the higher polyethylene oxides along with one or more of the above mentioned humectant polyols act synergistically to plasticize the skin or mucous tissue and provide a high degree of lubricity for enhancing the act of coitus.

It is well recognized that the human female may often suffer extreme discomfort because of dryness in the vaginal area. The causes of this dryness may be due to a variety of conditions that may occur following childbirth, following menstruation, at or after menopause, after a hysterectomy, or this may occur due to other hormonal disturbances. All of these discomforts can be alleviated by the application of my tissue lubricant.

My lubricant is very easy to apply and use. A few drops on the finger tips can be applied directly to the cervix and vaginal area. Also it can be applied by any of a wide variety of droppers or mechanical applicators, which themselves may be either single or multiple use items.

Because of the highly lubricating and tissue-conditioning characteristics of my lubricant, I have further found them to be unusually useful as shaving aids by lubricating the facial tissue, hair, and the razor blade and in this way doing a better job of cutting the beard. The lubricant is very effective even when applied directly to the dry skin of the face or body and can be used to facilitate shaving directly with a blade in the normal manner. However, I have found that it may be preferable to first wash with soap and water and then apply the lubricant to the pre-wetted surface. An alternative method is to use my lubricant in conjunction with any of the usual shaving creams or foams, thereby enhancing the comfort of the shave. Still another alternative is to combine my lubricant with the standard soap solution or aerosol cream so that it can be delivered from a pressurized container. Such a system would be capable of delivering a more stable foam with a very high lubricating capability.

I have found that my lubricants are also effective as a dermatological emollient and as a skin surface treatment, protecting the treated area from contact with air and from incidental surface irritation. The lubricant also has a number of other applications including use as a contact fluid for ultrasonic treatment of body tissue (the lubricating characteristics makes for smoother contact and movement over the body surface), as a lubricant for rectal and vaginal insertion of medical instruments, and it is useful in the removal of cosmetics.

DESCRIPTION OF THE PREFERRED EMBODIMENT

It is well known in the art that high molecular weight polyethylene oxides (molecular weights of 100,000 to 5,000,000) can readily be dissolved in aqueous systems by first dispersing the polymer in a non-solvent water soluble organic solvent and then slowly pouring this dispersion into well-stirred water. Warming the system above ambient temperature may be necessary to dissolve the parabens. According to my invention, I first disperse the polyethylene oxide into one or more polyhydroxy humectants that I have selected as being beneficial to the conditioning of body tissue. In the practice of my invention I have found it convenient to first dissolve any stabilizers or sterilizing inhibitors against bacterial, mold or fungal growth in the humectant solvent. In particular I have found that the methyl and propyl esters of parahydroxy benzoic acid are very effective for this purpose. These esters are known as methyl and propyl parabens, respectively. However other inhibitors or stabilizers may also be used, as for example, the alkyl quaternary ammonium halides or other inhibitors acceptable for cosmetic or pharmaceutical or food use. After the methyl and propyl parabens have been dissolved, along with any other organic compounds, such as anti-tack or anti-sticking agents, the requisite quantity of polyethylene oxide is stirred in. The amount of polyethylene oxide to be used can vary over a wide range and this depends upon the molecular weight of the polymer selected and the desired viscosity of the final lubricating solution. I have found that the ultimate concentration may be as high as 10 percent for a polymer with a molecular weight of 100,000 and it may be as low as 0.2 percent for a polymer in the molecular weight range of 4 to 5 million. For purposes of convenience and economy, I prefer to use ethylene oxides with molecular weights ranging from about 900,000 to 4,000,000 in concentrations from about 2.5 percent downward to about 0.5 percent.

In my formulations it is important to have a relatively high proportion of humectant polyols. These may range in concentrations from about 3 to 12 percent of the total system. From a practical standpoint I have found that the polyol concentration may conveniently be of the order of 5 to 9 percent of the total system.

As anti-tack or anti-sticking agents I have found that a wide variety of compounds can be used. Generally those compounds having a high degree of water solubility or water dispersibility are preferred. Such anti-sticking agents are not necessary for the proper functioning of my invention, but may be added to suit personal preferences or aesthetics. As anti-tack or anti-sticking agents I have found that the polyethoxylated sorbitan monoalkanoates are very effective. These are compounds such as the lauryl, myristyl, palmityl, oleyl and stearyl esters of polyethoxylated sorbitans, where the ethoxyl groups may range from about 15 to 30 in chain length. Similarly the ethoxylated glycerol monoalkanoates may also be used as well as the glyceryl monoalkanoates. The amounts to be added are limited only as to their degree of water solubility. However, as I have previously stated, it is not at all necessary to add anti-tack agents when some of the higher polyols of the humectant category are used in the formulation. Thus, I have found that stickiness is inhibited when sorbitol or any of the higher hydrogenated sugars are used in the formulation.

When the solution described above is used as a vaginal lubricant to aid in coitus, an alternative embodiment includes the addition of a spermicide for the inhibiting of pregnancy The water based lubricant can be combined with spermicidal creams, solutions and foams to provide excellent vaginal wetting characteristics, spermicidal dispersion, and relatively easy clean-up. The water based nature of this lubricant ideally suits it for use with latex condoms.

For the purpose of illustrating the preparation of my new tissue lubricants, the following examples are presented but they are in no way to be considered limiting.

EXAMPLE 1

About 1.3 g of methyl paraben and 0.7 g of propyl paraben were dissolved in 85 g of glycerol. Then 20 g of 900,000 molecular weight polyethylene oxide was dispersed in the cooled glycerol solution. This in turn was carefully added to 900 ml water stirred in a conventional mixing bowl. After ½ hour of intermittent stirring, solution was complete and it was bottled for storage

EXAMPLE 2

About 1.3 g of methyl paraben and 0.7 g of propyl paraben were dissolved with warming in 90 g glycerol. Then 10 g of about 4,000,000 molecular weight polyethylene oxide was dispersed in the cooled glycerol solution. This dispersion was slowly poured in a thin stream into 900 ml water, stirred with one blade of a conventional mixer in a mixing bowl. Within ½ hour of intermittent stirring, the solution was complete. This solution was then divided in several portions as follows:

a. To 100 ml of the above solution was added 0.5 ml of sorbitan monolaurate. This gave an excellent lubricant with very little tackiness on drying.

b. To 100 ml of the above solution was added 0.5 ml of sorbitan mono-oleate. This gave an excellent lubricant solution with reduced tackiness on drying.

c. To 100 ml of the above solution was added 0.4 ml of polyethoxylated sorbitan monolaurate and 0.4 ml of polyethoxylated sorbitan mono-oleate. This yielded an excellent lubricant solution with little or no tackiness on drying.

d. To 100 ml of the above solution was added 1.0 ml of polyethoxylated sorbitan mono-oleate. This yielded an excellent lubricant solution with little or no tackiness on drying.

EXAMPLE 3

In this case a higher viscosity lubricant was prepared. About 1.3 g methyl paraben and 0.7 g propyl paraben were dissolved with warming in 90 g of glycerol. Then to the cooled solution was added 12 g of 4,000,000 molecular weight polyethylene oxide and the mixture was thoroughly stirred for dispersion. This dispersion was then slowly poured, in a thin stream, into 900 ml water and stirred with one blade of a conventional mixer in a bowl. Within ½ hour of intermittent mixing the solution was complete. To the clear solution was added 12 g polyethoxylated sorbitan monostearate to yield an excellent lubricant solution with little or no tack.

EXAMPLE 4

Here a lower concentration of polyethylene oxide was used and still yielded a very desirable viscosity lubricating solution. About 0.65 g methyl paraben, 0.35 g propyl paraben and 3.0 ml of polyethoxylated sorbitan monostearate were dissolved with warming in 45 g glycerol. To this cooled solution was added 4 g polyethylene oxide (4,000,000 molecular weight). This dispersion was then poured in a thin stream into 450 ml water, which was well stirred. After ½ hour of intermittent stirring a clear lubricant solution was obtained, with little or no tackiness on drying.

EXAMPLE 5

About 0.65 g methyl paraben and 0.35 g propyl paraben were dissolved in 30 g heated glycerol and to this was added 15 g of a 70% solution of a hydrogenated higher sugar (e.g., Lonza, Inc.-Polyol 7000). To this cooled solution was added 4.0 g of 4,000,000 molecular weight polyethylene oxide. This dispersion was then poured, in a thin stream, into 450 ml of well stirred water to yield a clear solution, having excellent mucosal tissue lubricating properties, with little or no tackiness on drying.

EXAMPLE 6

About 0.65 g of methyl paraben and 0.35 g of propyl paraben were dissolved with heating in 30 g glycerol and then to this was added 15 g 70% sorbitol solution. To this cooled mixture was added 3.5 g of 4,000,000 molecular weight polyethylene oxide and the mixture was well stirred. This dispersion was then poured in a thin stream into 450 ml well stirred water. Solution was straightforward and yielded an excellent lubricant solution with little or no tackiness on drying.

EXAMPLE 7

The lubricant solution of Example 2, above, having a polyethylene oxide concentration of about 1% was diluted with varying proportions of water and each concentration was tested for lubricity. It was found that solutions having polyethylene oxide concentrations (molecular weight 4,000,000) as low as 0.2% still had fair lubricating characteristics.

In the examples I have cited above, lubricant solutions were prepared which had enhanced lubricating characteristics for body tissues. They are particularly useful in overcoming vaginal dryness and provide tissue conditioning as well. They are further useful as a shaving aid either by themselves or in conjunction with soap as in a shaving cream, foam or gel.

I claim:

1. A composition for lubricating body tissue consisting of:
   from about 0.2 to about 10 weight percent, based on total weight of the composition, of a polyethylene oxide, wherein the molecular weight of the polyethylene oxide ranges from about 100,000 to about 5,000,000;
   from about 5 to about 9 weight percent, based on total weight of the composition, of a humectant polyol solvent, selected from the group consisting of glycerol, propylene glycol, and sorbitol; and
   water.

2. The composition as in claim 1, wherein the molecular weight of the polyethylene oxide ranges from about 900,000 to about 4,000,000 and the concentration of the polyethylene oxide ranges from about 0.5 to about 2.5 weight percent, based on total weight of the composition.

3. The composition as in claim 1, wherein the molecular weight of the polyethylene oxide ranges from about 4,000,000 to about 5,000,000 and the concentration of the polyethylene oxide ranges from about 0.2 to about 1.0 weight percent, based on total weight of the composition.

4. The composition as in claim 1, wherein the molecular weight of the polyethylene oxide is about 100,000 and the concentration of the polyethylene oxide ranges from about 5 to about 10 weight percent based on total weight of the composition.

5. A composition for lubricating body tissue consisting of:
   from about 0.2 to about 10 weight percent, based on total weight of the composition, of a polyethylene oxide, wherein the molecular weight of the polyethylene oxide ranges from about 100,000 to about 5,000,000;
   from about 5 to about 9 weight percent, based on total weight of the composition, of a humectant polyol solvent, selected from the group consisting of glycerol, propylene glycol, and sorbitol; and
   an anti-stick agent wherein the anti-stick agent is selected from the group consisting of polyethoxylated sorbitan monoalkanoates, in concentrations up to the limit of water solubility of the anti-stick agent; and
   water.

* * * * *